United States Patent [19]

Garabedian

[11] Patent Number: Plant 5,453

[45] Date of Patent: Apr. 30, 1985

[54] PLUM TREE, "EARLY GAR ROSA"

[76] Inventor: John M. Garabedian, 3104 E. Huntington Blvd., Fresno, Calif. 93702

[21] Appl. No.: 535,736

[22] Filed: Sep. 26, 1983

[51] Int. Cl.[3] ..... A01H 5/03

[52] U.S. Cl. ..... Plt./38

[58] Field of Search ..... Plt./38

*Primary Examiner*—Robert E. Bagwill

*Attorney, Agent, or Firm*—Huebner & Worrel

[57] ABSTRACT

A plum tree generally similar to the Santa Rosa plum tree (unpatented) which it most nearly resembles, ripening twenty days earlier than the Santa Rosa, and bearing fruit having medium red skin and mild, delicately-flavored flesh.

1 Drawing Figure

BACKGROUND OF THE NEW VARIETY

The present invention relates to a new and distinct variety of plum tree broadly characterized by its productive, regular bearing of uniformly medium-sized fruit which has firm flesh which clings to the stone, and ripens twenty days earlier than the fruit of the unpatented Santa Rosa plum tree, which it most nearly resembles.

The factors contributing toward the commercial acceptance and success of any variety of plum tree are myriad. However, it is well known that the visual appearance of a plum is one of the primary motivating elements involved in a consumer's decision to purchase one type of plum rather than another. Further, it is well known that a plum that combines the desirable characteristic of visual asthetic appeal with the complementary attribute of having firm, meaty flesh of delicate flavor, is one which possesses a strong chance of becoming the object of repeated purchases by individual consumers thereof.

It has long been recognized as desirable to provide a plum tree variety which bears fruit having these desirable characteristics, and further having a uniform, symmetrical shape and attractive, even coloration. This is particularly so when such a plum ripens earlier than the plums sharing generally similar characteristics, thus affording the new variety an advantage in competition with other, similar varieties. Such early ripening also benefits consumers by extending the period during which consumers can avail themselves of several varieties having general characteristics in common.

ORIGIN AND ASEXUAL REPRODUCTION OF THE NEW VARIETY

My new variety of plum tree was discovered by me in 1968 as a seedling of unknown origin. The seedling was discovered on a ranch which was then and is now owned by me and which is located at the corner of Church and Greenwood Avenues, near the City of Sanger, in the County of Fresno, in the State of California.

I continued to observe the young seedling and asexually reproduced it in 1971 by budding it onto seedling stock. Such asexual reproduction was first conducted on a ranch then and now owned by me at the corner of Kings Canyon Road and Fowler Avenue, in the City of Fresno, in the County of Fresno, in the State of California. Fruit and tree characteristics of plum trees resulting from such budding proved to be identical to those of the original new growth.

SUMMARY OF THE NEW VARIETY

The instant variety of plum tree is generally characterized by bearing uniformly medium-sized fruit, having nearly full colored, medium red skin, and which ripens approximately twenty days earlier than the fruit of the unpatented Santa Rosa plum tree, which it most nearly resembles. The fruit of the instant variety further distinguishes itself from the Santa Rosa plum by its larger average size and firmer flesh. Additionally, the tree of the present variety is more vigorous than that of the Santa Rosa.

The fruit of the new variety is uniformly medium in size, and is uniform to slightly variably symmetrical in form. The fruit has firm, meaty flesh, mild and delicate in flavor, and adheres to the stone over the entire surface thereof.

The new variety is especially characterized by its nearly fully colored, medium red skin, and its large, vigorous tree which is a regular, productive bearer of its fruit.

BRIEF DESCRIPTION OF THE DRAWING

The accompanying drawing is a color photograph of a representative twig bearing a plum with the bloom characteristic of the new variety and bearing leaves characteristic of the new variety; three plums, two showing the base aspect, and one showing the suture aspect; and a plum divided to show the flesh color and the stone.

DETAILED DESCRIPTION

Referring more specifically to the pomological details of this new and distinct variety of plum tree, the following characteristics have been observed under the ecological conditions prevailing at the designated orchard in Fresno County, Calif. All of the color code plate indications are by reference to the Maerz & Paul *Dictionary of Color,* except where common terms of color definition are employed.

TREE

Size: Large, vigorous.

Figure: Upright, spreading, open, vase formed in accordance with usual pruning practices.

Productivity: Productive, regular bearer.

Trunk:
*Thickness.*—Medium.
*Texture.*—Medium.
*Color.*—Bark (Plate 16-A-6) Taupe.
*Striations.*—(Plate 15-10-C), Madrid Saddle Plus.

Branches:
*Thickness.*—Medium.
*Texture.*—Medium.
*Color.*—Brown to gray, with light brown striations.
*Lenticels.*—Medium, large-sized, inconspicuous.

Leaves:
*Shoot.*—Size — Medium; length 12.66±0.86 cm; width 4.64±0.29 cm. Shape — Oval to slightly obovate; accuminate pointed, medium thickness. Color — Medium to dark green; upper surface, (Plate 24-11-7); lower surface, (Plate 22-G-7). Texture — Nearly smooth. Margin — Crenate. Petiole — Medium length, 1.87±0.20 cm.; medium thickness. Glands — Average number 2, small, green, globose glands at opposite sides of base of blade. Stipules — Long, linear, ephemeral.
*Spur.*—Size — Length 11.46±1.58 cm.; width 3.66±0.44 cm. Shape — Obovate to nearly spatulate; apex blunt accuminate; base accuminate. Color — Medium to dark green. Texture — Nearly smooth. Margin — Crenate. Petiole — Medium length, 1.88±0.31 cm.; medium thickness. Glands — Usually zero, rarely one at base of blade; small, globose, green, lacking stipules.

Buds: Small, short; plump; free; glabrous; brown.

Flowers:
*Dates of bloom.*—In 1982, first bloom on Feb. 25, 1982; full bloom, Mar. 9, 1982; dates of bloom medium compared with other varieties.
*Size.*—Medium to large.
*Color.*—White.

FRUIT

Maturity: Firm ripe approximately May 25.

Size: Uniformly medium; axial diameter — 4.82±0.19 cm.; transverse diameter in suture plane — 5.16±0.13 cm.; diameter in cheek plane — 5.37±0.15 cm.

Form: Uniformly to slightly variably symmetrical.
*Cheek.*—Truncate, broad oval, occasionally cordate.
*Suture.*—Broad oval to slight oblate.
*Axial.*—Nearly round; suture side inconspicuously flattened.

Suture: Inconspicuous, very shallow groove extending nearly uniformly from base to apex.

Ventral surface: Rounded slightly; lipped throughout; lips equal, low, broad, one often higher at apex.

Stem cavity: Flaring, rounded; somewhat elongated in suture plane with suture showing on one side; depth — 1.00±0.10 cm.; breadth — 2.13±0.14 cm.; markings — smooth, even.

Base: Broadly rounded to truncate.

Apex: Short, rounded to truncate, slightly depressed.

Pistil point: Apical.

Skin: Medium thickness; medium to tough toughness; slightly bitter; tenacious to flesh; no tendency to crack in dry season; down — wanting.
*Color.*—Nearly full colored; medium red (Plate 4-J-6) Ceres.
*Bloom.*—Scant, light bluish-gray (Plate 53-B-4).
*Ground color.*—Light greenish-yellow (Plate 18-K-2).

Flesh:
*Color.*—Light yellowish-amber (Plate 10-I-4) Pond lily, diffused red next to skin.
*Amygdalin.*—Wanting.
*Juice.*—Moderate.
*Texture.*—Firm, fine, meaty.
*Fibers.*—Few, fine.
*Ripening.*—Even.
*Flavor.*—Sub-acid, mild, delicate.
*Aroma.*—Wanting.
*Eating quality.*—Good.

Stone: Cling; adheres to flesh over entire surface.
*Size.*—Large; length — 2.41±0.13 cm.; breadth — 1.87±0.08 cm.; thickness — 1.01±0.02 cm.
*Form.*—Cheek aspect oval to slightly obovate, slightly necked at base, neck lightly ridged and furrowed.
*Base.*—Nearly straight; hilum — narrow, oval.
*Apex.*—Rounded with a blunt tip.
*Sides.*—Nearly equal.
*Surface.*—Irregularly lightly furrowed near base.
*Ventral edge.*—Medium, usually low, often eroded; lateral grooves variable, but usually deep, broad, especially basally; often shallow apically.
*Dorsal edge.*—Narrow with shallow to narrow groove toward base and apex.
*Color.*—Light tan (Plate 9-B-4).
*Tendency to split.*—Slight.

Use: Dessert.

Keeping quality: Good.

Resistance to insects: Medium.

Resistance to diseases: Medium.

Shipping quality: Good.

Although the new variety of plum tree possesses the described characteristics under the growing conditions prevailing in Fresno County, Calif., in the central portion of the San Joaquin Valley, it is to be understood that variations of the usual magnitude in characteristics incident to changes in growing conditions, fertilization, pruning and pest control are to be expected.

Having thus described and illustrated my new variety of plum tree, what is claimed as new and desired to be secured by Letters Patent is:

1. A new and distinct variety of plum tree substantially as illustrated and described and broadly characterized by the ripening of its fruit approximately twenty days earlier than that of the unpatented Santa Rosa plum tree, which it most nearly resembles, but further differing therefrom in its regular and productive bearing of fruit having larger average size and firmer flesh when eating ripe, and the greater vigor of its tree.

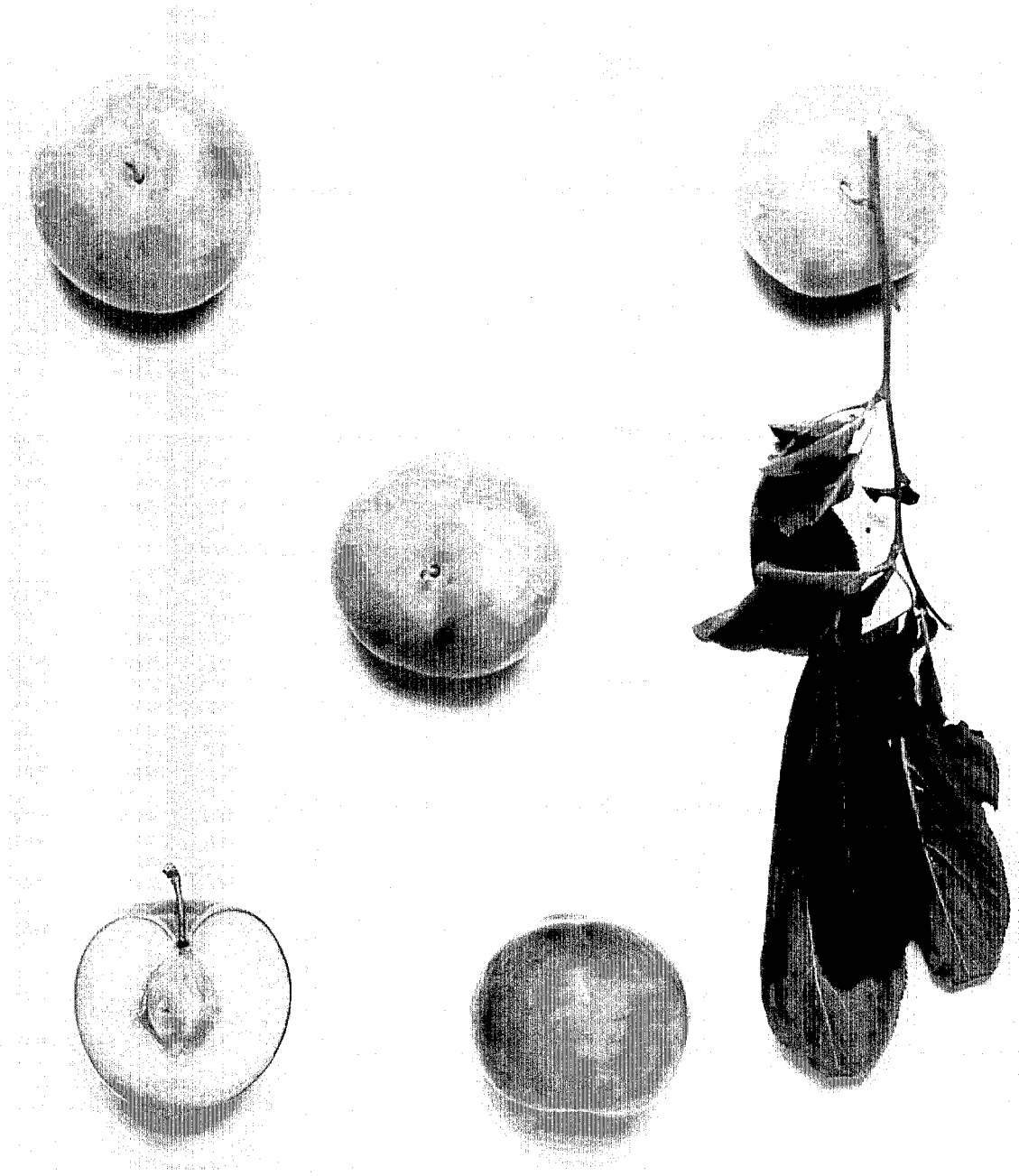

* * * * *